United States Patent [19]

Yoshida

[11] Patent Number: Plant 7,740

[45] Date of Patent: Dec. 10, 1991

[54] AFRICAN VIOLET NAMED DAYNA

[76] Inventor: Eiichi Yoshida, P.O. Box 4836, Hayward, Calif. 94540-4836

[21] Appl. No.: 524,122

[22] Filed: May 14, 1990

[51] Int. Cl.[5] ..... A01H 5/00

[52] U.S. Cl. ..... Plt./69

[58] Field of Search ..... Plt./69

*Primary Examiner*—James R. Feyrer

[57] ABSTRACT

A new and distinct cultivar of African violet plant named 'Dayna' for potted plant culture particularly distinguished by its year 'round blooming capability, its profuse production of white with purple-violet edged flowers, and its compact growth with abundant foliage of solid green color which provides a spreading base and attractive backing for the clusters of blossoms.

1 Drawing Sheet

BACKGROUND OF THE NEW PLANT

This new variety of African violet plant was obtained by cross-pollenating the seed parent "Melodie" Rhonda and the pollen parent "Melodie" Farrah×"Melodie" Julianne Sport. The seed pods of the pollenated plants were used as the generic basis for initiating further propagation trials. The specified plant was a selection from among the initial 90 selected plants remaining from the initial cross. The plant of this disclosure was selected on the basis of a number of outstanding characteristics in combination which included the plant having contrasting top and bottom leaf coloration without red tones, with leaves of uniform shape borne by long, ponderous leaf stems. Leaves and leaf stems lack any red coloration and contrast with multicolored flower parts. The further displays a generous number of flowers of generally single and attractive, rounded shape with slightly ruffled petal peripheral portions. The flowers are nearly flat when fully open and are supported on peduncles that are strong but which lean. Petals are predominately white with purple-violet margin color which appealingly contrasts with the white central petal portions.

This selection was subsequently denominated "Dayna". I have asexually reproduced 'Dayna' by take leaf cuttings to start plants in the conventional manner for *Saintpaulia ionantha* as well known to the grower. Clones of this original selection have proven to be substantially identical to the parent plant in all distinguishing characteristics and establish that 'Dayna' is genetically stable.

BRIEF DESCRIPTION OF THE DRAWING

Sheet one is a full color photographic view of the plant in bloom, the colors shown being as nearly true as it is reasonably possible to obtain by conventional photographic procedures.

DESCRIPTION OF THE PLANT

The following is a detailed description of my new African violet plant with the color designation being accorded to the R.H.S. Colour Chart published by The Royal Horticultural Society of London, England, with collaboration by the British Colour Council.

THE PLANT

Name: African Violet named Dayna.
Origin: Seedling.

Parentage:
- *Seed parent.*—Saintpaulia "Melodie" Rhonda.
- *Pollen parent.*—Saintpaulia "Melodie" Farrah×-Saintpaulia Julianne Sport.

Classification:
- *Botanic.*—*Saintpaulia ionantha.*
- *Commercial.*—African Violet.

Form: Rosette arrangement.
Height: 8 to 10 cm.
Growth: Moderate, petioles at first upright, becoming horizontal with age.
Size: Medium, to 22 cm. in diameter.
Mutation prone: Slight, some variation occurs in the relative amount of red and white pigment in the petal.
Foliage:
- *Shape.*—Ovate, slight cordate base, rounded tip, slight crenate margin.
- *Length.*—7 to 8 cm. on mature leaves.
- *Width.*—6 to 7 cm. on mature leaves.
- *Color.*—Upperside: Medium green. Underside: Pale green.
- *Texture.*—Upperside: Pubescent. Underside: Puberulent.
- *Ribs and veins.*—Pronounced, pinnate.
- *Petiole.*—*Flattened above, pubescent, pale green.*

THE FLOWER

Blooming habit: Continuous and abundant under optimum growing conditions.
Number: Seven to nine per peduncle.
Size of Flower: Each flower is approximately 4 to 5 cm. in diameter.
Color: Central parts are White, R.H.S 155C. Edges of petals are Purple-Violet, R.H.S 80A.
Type: Single.
Petals: Five per individual flower with ruffled margins, bicolored.
Texture: Smooth and slightly flexible.
Appearance: Upperside glabrous, lowerside slightly puberulent.
Peduncles: 7 to 8 cm. in height, pubescent, light green.
Inflorescence: Cyme, upright, above the foliage.
Calyx: Quinquepartite, light green, pubescent.
Persistence: Flowers do not drop.
Fragrance: None.

REPRODUCTIVE ORGANS

Stamen: Usually two per flower.

*Anthers.*—Bright yellow, basifixed, two per filament.

*Filament.*—c. 0.4 cm. in length.

*Pollen.*—Light yellow.

Pistils: Normally one per flower.

*Stigma.*—Visible and accessible, becoming swollen when receptive and exuding a droplet of clear liquid.

*Style.*—c. 0.7 cm. in length.

*Ovary.*—Superior.

I claim:

1. A new and distinct cultivar of African violet named 'Dayna', as described and illustrated, and particulary characterized by its single, delicate, variegated flowers mainly white with purple violet edges, and its year 'round blooming capacity which gives the plant a nearly continuous beauty.

* * * * *

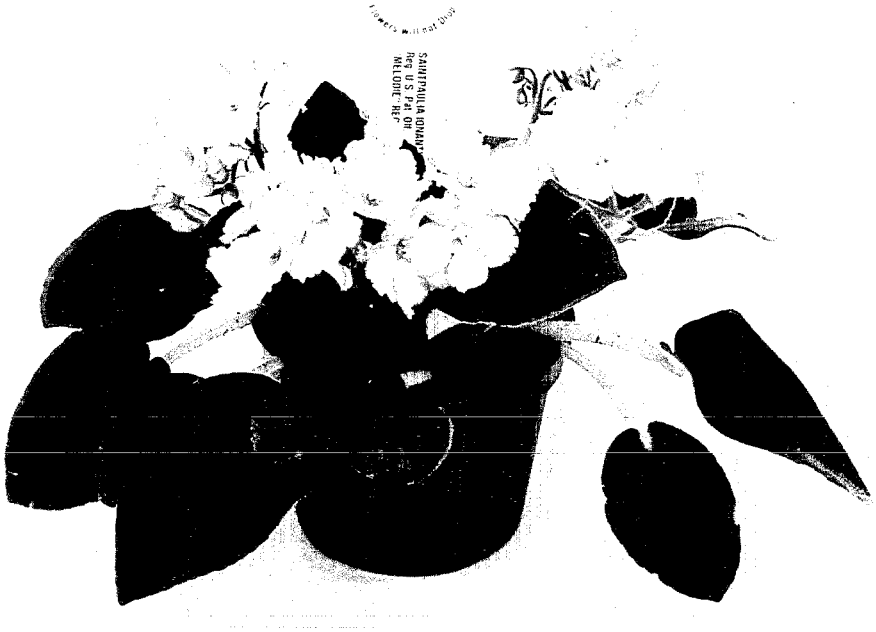
Flower Natural Size
SAINTPAULIA IONANTHA
Reg U.S. Pat. OFF
MELODIE REF